US009486416B2

(12) United States Patent
Winchester et al.

(10) Patent No.: US 9,486,416 B2
(45) Date of Patent: Nov. 8, 2016

(54) EMULSION-BASED PROCESS FOR PREPARING MICROPARTICLES AND WORKHEAD ASSEMBLY FOR USE WITH SAME

(75) Inventors: Gary Winchester, Warrior, AL (US); Peter Markland, Birmingham, AL (US)

(73) Assignee: Evonik Corporation, Parsippany, NJ (US)

( * ) Notice: Subject to any disclaimer, the term of this patent is extended or adjusted under 35 U.S.C. 154(b) by 39 days.

(21) Appl. No.: 12/968,708

(22) Filed: Dec. 15, 2010

(65) Prior Publication Data

US 2011/0204533 A1 Aug. 25, 2011

Related U.S. Application Data

(60) Provisional application No. 61/288,973, filed on Dec. 22, 2009.

(51) Int. Cl.
*A61K 9/50* (2006.01)
*B01F 3/08* (2006.01)
(Continued)

(52) U.S. Cl.
CPC .......... *A61K 9/5031* (2013.01); *A61K 9/5089* (2013.01); *B01F 3/0807* (2013.01); *B01F 5/0693* (2013.01); *B01F 7/00241* (2013.01); *B01F 13/1033* (2013.01)

(58) Field of Classification Search
CPC .......... A61K 8/04; A61K 8/066; A61K 8/11; A61K 9/16; A61K 9/4833; A61K 9/50; B82Y 30/00; B82Y 5/00; B82Y 40/00; C08F 2/22; B01D 5/006; B01F 3/0807; B01F 5/0682; B01F 5/0693; B01F 15/00

USPC .................. 428/402–402.24, 403, 404, 407; 427/389.9, 213.3–213.36, 483, 256; 424/400, 408, 450, 451, 455, 93.7, 424/184.1, 497, 489, 501, 490, 491, 492, 424/493, 494, 495; 264/534, 4–4.7

See application file for complete search history.

(56) References Cited

U.S. PATENT DOCUMENTS 2,247,439 A 7/1941 Hayes
2,578,805 A 12/1951 Johnson
(Continued)

FOREIGN PATENT DOCUMENTS

BR 1120120152009 12/2010
CA 2784287 12/2010
(Continued)

OTHER PUBLICATIONS

International Search Report with Written Opinion issued on Aug. 23, 2011 for Intl. App. No. PCT/US2010/060473, filed Dec. 15, 2010 (Inventor—Winchester et al.; Applicant—Surmodics Pharmaceuticals, Inc.).

(Continued)

*Primary Examiner* — James J Seidleck
*Assistant Examiner* — S. Camilla Pourbohloul
(74) *Attorney, Agent, or Firm* — Linda S. Li; Jason S. Ngui; Bernard Lau

(57) ABSTRACT

The present invention relates to emulsion and double-emulsion based processes for preparing microparticles. The invention also relates to workhead assemblies for in-line flow-through mixing devices that can be used for mixing two or more fluids. The workhead assemblies can be used with the processes for preparing microparticles.

16 Claims, 11 Drawing Sheets

(51) Int. Cl.
  *B01F 5/06*  (2006.01)
  *B01F 7/00*  (2006.01)
  *B01F 13/10*  (2006.01)

(56) References Cited

U.S. PATENT DOCUMENTS

| | | | |
|---|---|---|---|
| 3,501,914 | A | 3/1970 | Asher |
| 4,476,148 | A | 10/1984 | Harris |
| 5,407,609 | A | 4/1995 | Tice et al. |
| 5,529,392 | A | 6/1996 | O'Donnell et al. |
| 5,540,499 | A | 7/1996 | Seeger |
| 5,635,216 | A | 6/1997 | Thompson |
| 5,843,334 | A | 12/1998 | Saheki et al. |
| 5,852,076 | A | 12/1998 | Serafin et al. |
| 5,869,103 | A | 2/1999 | Yeh et al. |
| 5,945,126 | A | 8/1999 | Thanoo et al. |
| 6,042,792 | A | 3/2000 | Shefer et al. |
| 6,291,013 | B1 | 9/2001 | Gibson et al. |
| 6,440,493 | B1 | 8/2002 | Gibson et al. |
| 6,499,389 | B1 | 12/2002 | Probst |
| 7,287,651 | B2 | 10/2007 | Myers et al. |
| 7,344,570 | B2 | 3/2008 | Moncrieff et al. |
| 2003/0094715 | A1* | 5/2003 | Suzuki et al. ............. 264/4.1 |
| 2004/0152788 | A1 | 8/2004 | Wu et al. |
| 2005/0056170 | A1 | 3/2005 | Koike et al. |
| 2006/0164912 | A1 | 7/2006 | Arnaud |
| 2007/0071825 | A1 | 3/2007 | Curdy et al. |
| 2007/0207211 | A1 | 9/2007 | Zeigerson |
| 2007/0294935 | A1 | 12/2007 | Waldron et al. |
| 2009/0104274 | A1* | 4/2009 | Khopade et al. ........... 424/490 |
| 2009/0162407 | A1 | 6/2009 | Biggs et al. |
| 2011/0135933 | A1* | 6/2011 | Shoko et al. .......... 428/402.2 |

FOREIGN PATENT DOCUMENTS

| | | |
|---|---|---|
| CN | 2010800644259 | 12/2010 |
| EP | 0172010 A2 | 2/1986 |
| EP | 0885615 A1 | 12/1998 |
| EP | 1115317 A1 | 7/2001 |
| EP | 1560641 A1 | 8/2005 |
| EP | 10843487.9 | 12/2010 |
| GB | 501675 A | 3/1939 |
| GB | 916757 A | 1/1963 |
| GB | 1231823 A | 5/1971 |
| GB | 2157744 A | 10/1985 |
| IN | 5340/DELNP/2012 | 12/2010 |
| JP | 11057456 A | 3/1999 |
| JP | 2003005453 A | 1/2003 |
| JP | PCT/US2010/060473 | 12/2010 |
| KR | 2012-7017983 | 12/2010 |
| RU | 2012130937 | 12/2010 |
| WO | WO-95/05939 A1 | 3/1995 |
| WO | WO-95/11009 A1 | 4/1995 |
| WO | WO-98/35654 A1 | 8/1998 |
| WO | WO-2005/070046 A2 | 8/2005 |
| WO | WO-2006/123359 A2 | 11/2006 |
| WO | WO-2008/009623 A1 | 1/2008 |
| WO | WO-2009/044926 A1 | 4/2009 |
| WO | PCT/US2010/060473 | 12/2010 |

OTHER PUBLICATIONS

Extended European Search Report, PCT/US2010060473, dated Jul. 24, 2013, six pages.

Freitas S et al, "Microencapsulation by solvent extraction/evaporation: reviewing the state of the art of microsphere preparation process technology", Journal of Controlled Release, Elsevier, Amsterdam, NL, vol. 102, No. 2, Feb. 2, 2005 (Feb. 2, 2005), pp. 313-332.

International Preliminary Report on Patentability issued on Jul. 5, 2012 for PCT/US2010/060473, filed Dec. 15, 2010 (Inventor—Winchester et al.; Applicant—Surmodics Pharmaceuticals, Inc.; pp. 1-6).

* cited by examiner

US 9,486,416 B2

EMULSION-BASED PROCESS FOR PREPARING MICROPARTICLES AND WORKHEAD ASSEMBLY FOR USE WITH SAME

CROSS-REFERENCE TO RELATED APPLICATIONS

This application claims the benefit of priority from U.S. Provisional Application No. 61/288,973, filed Dec. 22, 2009, the entire contents of which are incorporated herein by reference.

BACKGROUND

Microparticles are particles generally less than 2 millimeters in diameter and are typically spherical. Common microparticles generally comprise a matrix forming material, such as a polymer. A variety of substances can be encapsulated by microparticles. These substances can be released from the microparticle through various mechanisms, including controlled-release mechanisms wherein the substance passes through the microparticle matrix over time and also including rupture-release or degradation mechanisms wherein the microparticle matrix ruptures, degrades, or erodes over time to release the substance.

Several processes exist for preparing microparticles. Emulsion-based processes for making microparticles usually begin with the preparation of two separate phases: a first phase, typically referred to as a dispersed phase, which generally comprises a dispersion or solution of an agent, which is the substance to be encapsulated, in a dispersion or solution of polymer in a first solvent, and a second phase, typically referred to as a continuous phase, which generally comprises a second solvent that is at least partially immiscible with the first solvent of the dispersed phase. After the first and second phases are prepared, they are combined using dynamic or static mixing to form an emulsion, wherein microdroplets of the first phase are dispersed in the continuous phase. The microdroplets then are hardened to form microparticles that contain the agent. The hardening step is carried out by removal of the first solvent from the microdroplets, generally by either an extraction or evaporation process.

The emulsion forming step is often carried out using a mixing device. In one specific example, with reference to FIG. 1A, a mixing device comprises a rotor/stator workhead assembly 1100 having an inlet port 1101 for introducing liquid and solid 1104a materials, which constitute the combined dispersed and continuous phases, into the workhead assembly 1100. Liquid and solid 1104a materials are drawn into the workhead assembly 1100 by powerful suction created by a rotor element 1106 comprising rotor blades that is rotated by a shaft 1102. The rotor blades are positioned substantially perpendicular to a stator element 1107. Materials exit the workhead assembly at exit port 1103.

Referring now to FIG. 1B, as the liquid and solid 1104a materials are drawn into the workhead assembly 1100, centrifugal force created by the rotor element 1106 drives the materials toward the stator element 1107.

Referring now to FIG. 1C, the materials then pass through perforations in the stator element 1107 and are driven toward the periphery of the workhead assembly 1100. The materials are forced through the perforations of the stator element 1107 at a velocity that subjects the materials to intense hydraulic shear. The material then exits the workhead assembly at exit port 1103. The mixing action of the workhead assembly forces the dispersed phase into the continuous phase to form an emulsion comprising microdroplets of the dispersed phase in the continuous phases.

One disadvantage of using a workhead assembly such as the assembly shown in FIGS. 1A-C is that the overall microparticle preparation process can be low-yielding and can result in broad particle size distributions. Accordingly, a need exists for new mixing assemblies and processes using the mixing assemblies that overcome the disadvantages often encountered with typical mixing assemblies used in microparticle production processes. This need and other needs are satisfied by the present invention.

SUMMARY

In one aspect, disclosed is a process for making microparticles, comprising: (a) providing a process stream comprising (i) a dispersed phase comprising a first solvent having a polymer and an agent dissolved or dispersed therein; and (ii) a continuous phase comprising a second solvent that is partially or totally immiscible in the first solvent; (b) passing the process stream through a screen and into a mixing environment; such that during steps (a) or (b), microdroplets of the dispersed phase form in the continuous phase; and (c) at least substantially removing the first solvent from the microdroplets to form the microparticles.

In another aspect, disclosed is a process for making microparticles, comprising: (a) providing a process stream comprising: a primary emulsion comprising microdroplets of (i) a first dispersed phase comprising a first solvent having an agent dissolved or dispersed therein, and (ii) a second dispersed phase comprising a second solvent that is partially or totally immiscible in the first solvent and having a polymer dissolved or dispersed therein; and a continuous phase comprising a third solvent that is partially or totally immiscible in the second solvent; (b) passing the process stream through a screen and into a mixing environment; such that during step (a) or (b), a double-emulsion forms; and (c) at least substantially removing the second solvent from the double-emulsion to form the microparticles.

In still another aspect, disclosed is a workhead assembly for a non-static flow through mixer, comprising: a housing forming a mixing chamber and defining a fluid inlet port in communication with the mixing chamber and a fluid outlet port in communication with the mixing chamber; a screen mesh extending across the inlet port; and a rotor positioned within the housing between the screen and the fluid outlet port such that when the rotor is rotated, fluid is directed from the inlet port, through the screen mesh, to the outlet port.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1A:
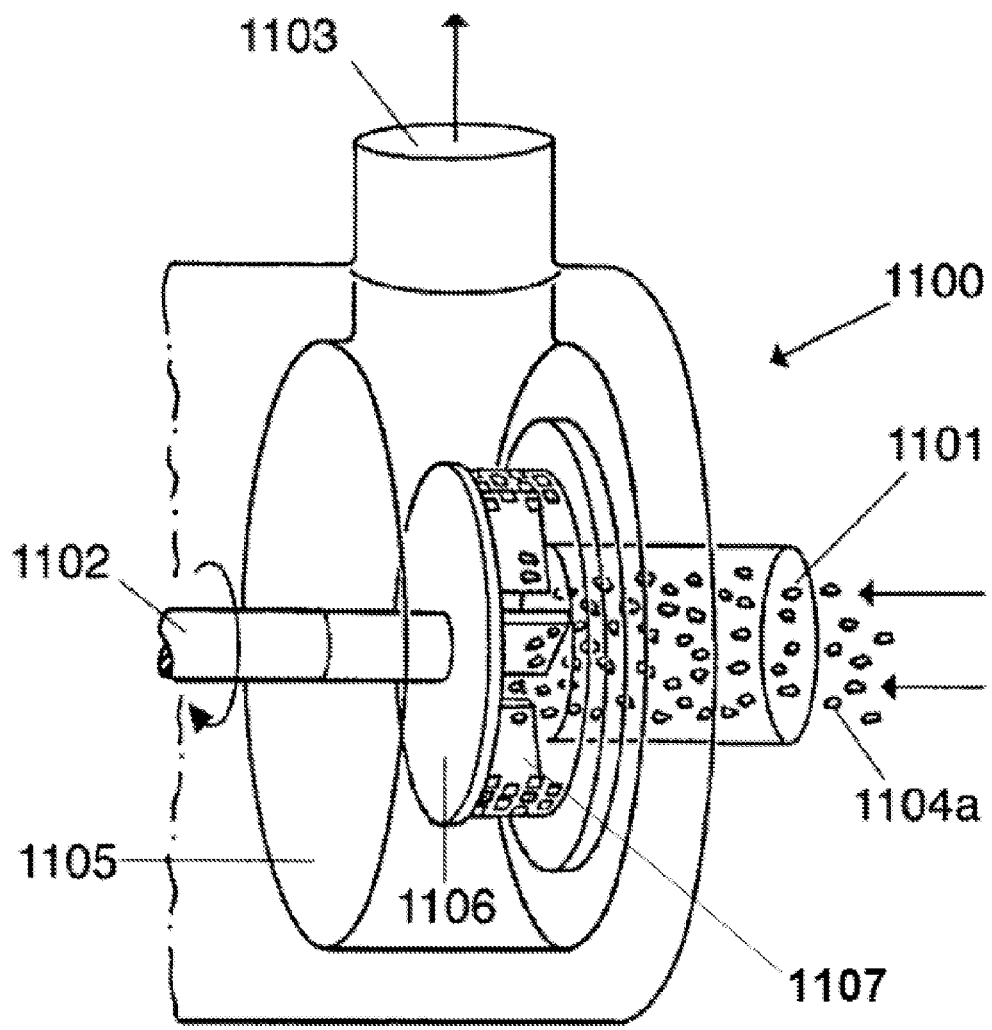
FIGS. 1A-C are drawings of a mixing process as performed using a conventional mixing head on a rotor/stator mixer.

Before the present compounds, compositions, composites, articles, devices and/or methods are disclosed and described, it is to be understood that the aspects described below are not limited to specific compounds, compositions, composites, articles, devices, methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "an agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

As used herein, a "screen" refers to a porous material through which the process stream of the invention can pass. The porosity of the screen can vary widely depending on the particular process, as will be discussed below.

As used herein, "mixing environment" refers to mixing conditions in which two or more fluids are mixed to blend the fluids in the process stream, for example to force a dispersed phase into a continuous phase to form an emulsion.

As used herein, a "non-static flow through mixer" refers to a mixer having elements that move within a flowing stream of fluids and/or solids.

In one aspect, the process of the invention comprises (a) providing a process stream comprising (i) a dispersed phase comprising a first solvent having a polymer and an agent dissolved or dispersed therein; and (ii) a continuous phase comprising a second solvent that is partially or totally immiscible in the first solvent; (b) passing the process stream through a screen and into a mixing environment such that microdroplets comprised of the dispersed phase dispersed in the continuous phase are formed either during step (a) or (b), or both; and (c) removing the first solvent from the microdroplets to form the microparticles.

In another aspect, the process of the invention comprises (a) providing a process stream comprising: a primary emulsion comprising microdroplets of (i) a first dispersed phase comprising a first solvent having a polymer and an agent dissolved or dispersed therein, and (ii) a second dispersed phase comprising a second solvent that is partially or totally immiscible in the first solvent; and a continuous phase comprising a third solvent that is partially or totally immiscible in the second solvent; (b) passing the process stream through a screen and into a mixing environment such that a double-emulsion forms during step (a) or (b) that comprises the first and second dispersed phases in the continuous phase; and (c) removing the first solvent from the double-emulsion to form the microparticles. Thus, the process of the invention can be used in both emulsion-based and double-emulsion based microencapsulation methods.

It has been surprisingly found that by first passing the process stream through a porous screen and then subjecting the process stream to a mixing environment, and in certain aspects, without a subsequent screen or perforated stator in the mixing environment itself, a number of advantages are realized. In contrast to a process utilizing a workhead of a typical in-line mixing device, such as those shown in FIGS. 1A-C, the disclosed process first passes the process stream through a porous screen which aids in microdroplet formation prior to the mixing step, and/or reduces particles of a certain size. In a typical mixing workhead, a process stream first enters a mixing environment without having first been screened and then is propelled by centrifugal force created by a rotor in the mixing device toward a stator and then passes through perforations in the stator (typically macro-perforations), as discussed above with reference to FIGS. 1A-C. This creates a high-shear environment and therefore leads a large population of fine particles, which can reduce yield and increase particle size distribution.

Without wishing to be bound by theory, it is believed that the processes of the invention reduce the energetics of the mixing process by producing a smaller population of very fine particles along with very large particles. Thus, the process is useful in providing a more narrow overall particle size distribution of the final microparticles. The process of the invention also provides better yields relative to conventional mixing. The mixing environment of the present invention is believed to cause less shear than the typical high-shear mixing environment created with mixers such as those depicted in FIGS. 1A-C.

According to the disclosed process, a process stream is first provided that comprises either the dispersed phase together with the continuous phase or a primary emulsion together with the continuous phase. The process stream is prepared by combining the dispersed phase or emulsion together with the continuous phase. Once combined, the mixture of dispersed phase or primary emulsion and the continuous phase may or may not be mixed. Likewise, upon providing the process stream, an emulsion may begin to form, prior to mixing.

The process stream is then passed through a screen, which is porous. Depending on the nature of the process, a variety of screens can be used, which generally will have a pore size ranging from 0.1 to 1000 μm or even larger, but preferably from about 1 to 400 μm. For example, in one aspect, the screen can comprise a range of nominal pore sizes, for example, a screen having a mesh size 14 (1.4 mm) to mesh size 500 (25 microns) to even higher mesh sizes (smaller nominal pore sizes).

The screen can comprise a variety of materials. In one aspect, the screen is a stainless steel mesh cloth or fabric having the desired pore size. To make such a screen, for example, a filter screen material can be cut out from a desired pore size, such as a 75 micron (200 mesh) test sieve that is typically used for sieving particles. An example of such a material is a FISHERBRAND U.S. Standard Stainless Steel Test Sieve. A similar stainless steel mesh fabric can be obtained commercially from Small Parts, Inc. (Miami Lakes, Fla.), which is a stainless steel mesh filter, (120 mesh or 200 mesh) and is of a plain weave design.

Other suitable screen materials include a variety of types of glass, metal, polymers, and inorganic materials, such as silica and alumina. Specific examples of such screens include sintered glass screens or plates, sintered metal screens or plates, and porous silica screens. Screens can also be prepared from porous filter membranes such as those made from hydrophobic or hydrophilic membrane materials, such as those comprising fluoropolymers, polytetrafluoro-ethylene, polyethylene, PVDF (polyvinylidene fluoride), PCTE, cellulose ester, mixed cellulose ester, nitrocellulose, nylon, polycarbonate, metals, silver, gold, stainless, silica, and alumina materials.

In other aspects, the screen comprises a metal material having a pore size ranging from about 1 to about 500 μm or higher, more preferably from about 10 to about 200 μm. In specific examples, the screen can have an average pore size of from about 50 to about 150 for example, 75 or 125 μm. The screen can be selected based on the desired end-use of the microparticle. For example, for a microparticle that can be injected into a living subject, smaller particle sizes can be desirable, and thus a smaller screen can be used.

In other aspects, the screen can be prepared from a tortuous matrix, such as in a mixed fibrous membrane of cellulose ester or nylon, a nonwoven matrix, or a sintered metal, or glass disk, or can be prepared from an etched design having relatively consistent diameter pores through a membrane surface such as precision-drilled organic and inorganic membranes, laser-drilled membranes, inorganic pores (for example, ANOPORE alumina membrane), and track-etched membranes (for example, NUCLEPORE membrane).

The process stream enters a mixing environment wherein the dispersed phase or the primary emulsion is mixed with the continuous phase. During the mixing step, the dispersed phase or the primary emulsion is driven into the continuous phase to form microdroplets of the dispersed phase or to form a double-emulsion. Microdroplet formation is aided by the screening step, as discussed above. A variety of methods exist to create a mixing environment. Suitable devices that can be used in the mixing step include but are not limited to static mixers and dynamic mixers. Such mixers include, for example, agitators, homogenizers, sonication devices, and other process equipment known in the art.

In a further aspect, mixing can be performed by pumping together the dispersed phase or the primary emulsion and the continuous phase through a length of pipe or tubing at conditions sufficient to create adequate mixing, i.e. enough turbulence to induce or enhance emulsion formation.

Restriction plates (flow constrictors) and filters, can also be used to create the required mixing environment. Other suitable mixers include non-motorized turbines and flow indicators, such as a ball indicator. Another example is the workhead of a flow-through mixer, such as those on commercially available mixers, e.g., a SILVERSON mixer (SILVERSON Machines Inc., East Longmeadow, Mass., U.S.A.), or more preferably the disclosed workhead of the invention, which is described below. The SILVERSON mixer can be a standard commercially-available mixer without a screen and with a stator after the rotor, or one that has been modified by removing the stator and placing a screen across the inlet port, as will be discussed below. In one aspect, once the process stream first passes through a screen, it does not pass through a subsequent screen after the mixing environment, or in the mixing environment but after the first screening step. In further aspects, the process stream is passed through two or more screens, which can be same or different, prior to entering the mixing environment.

In the disclosed double-emulsion process, the primary emulsion can be formed analogously, i.e., by mixing a dispersed phase and a continuous phase together. In one aspect, the primary emulsion can first be formed using the disclosed process, and then a double emulsion can be formed using the same disclosed process. Alternatively, the primary and double-emulsions can be created using different mixing methods.

Figure 1B:
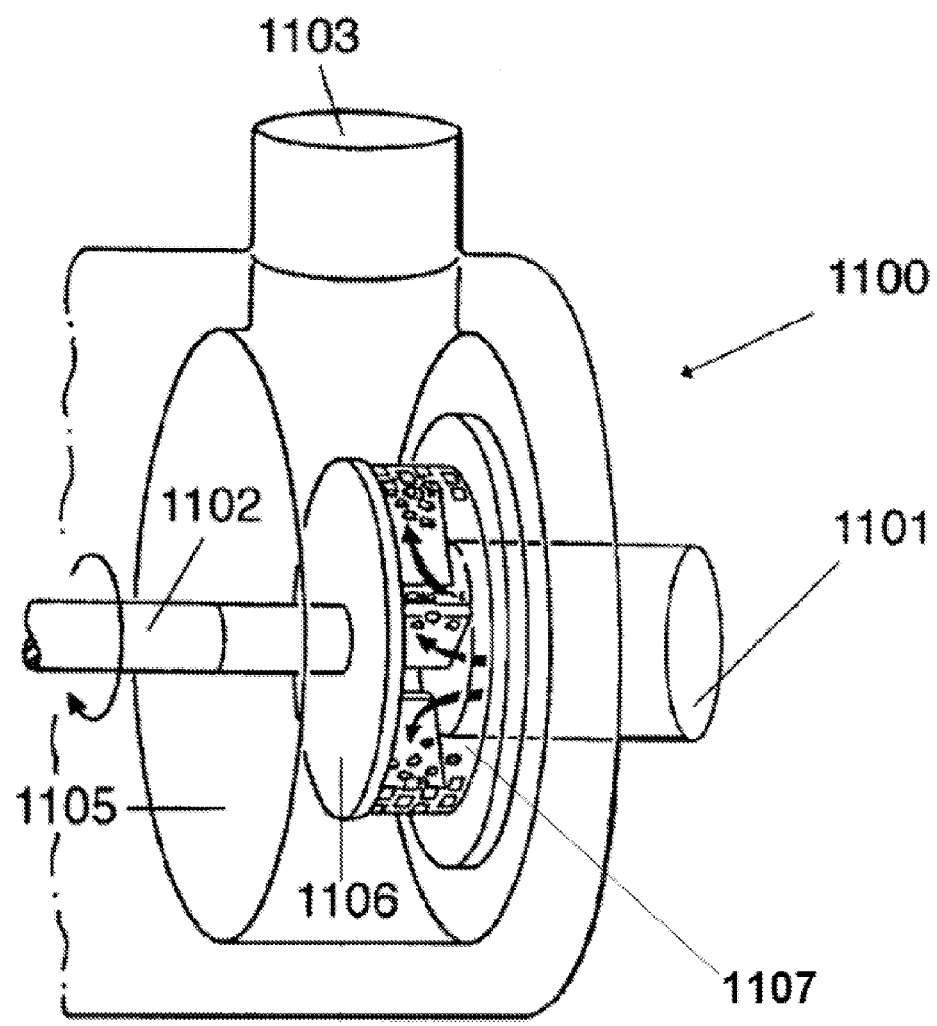
Figure 1C:
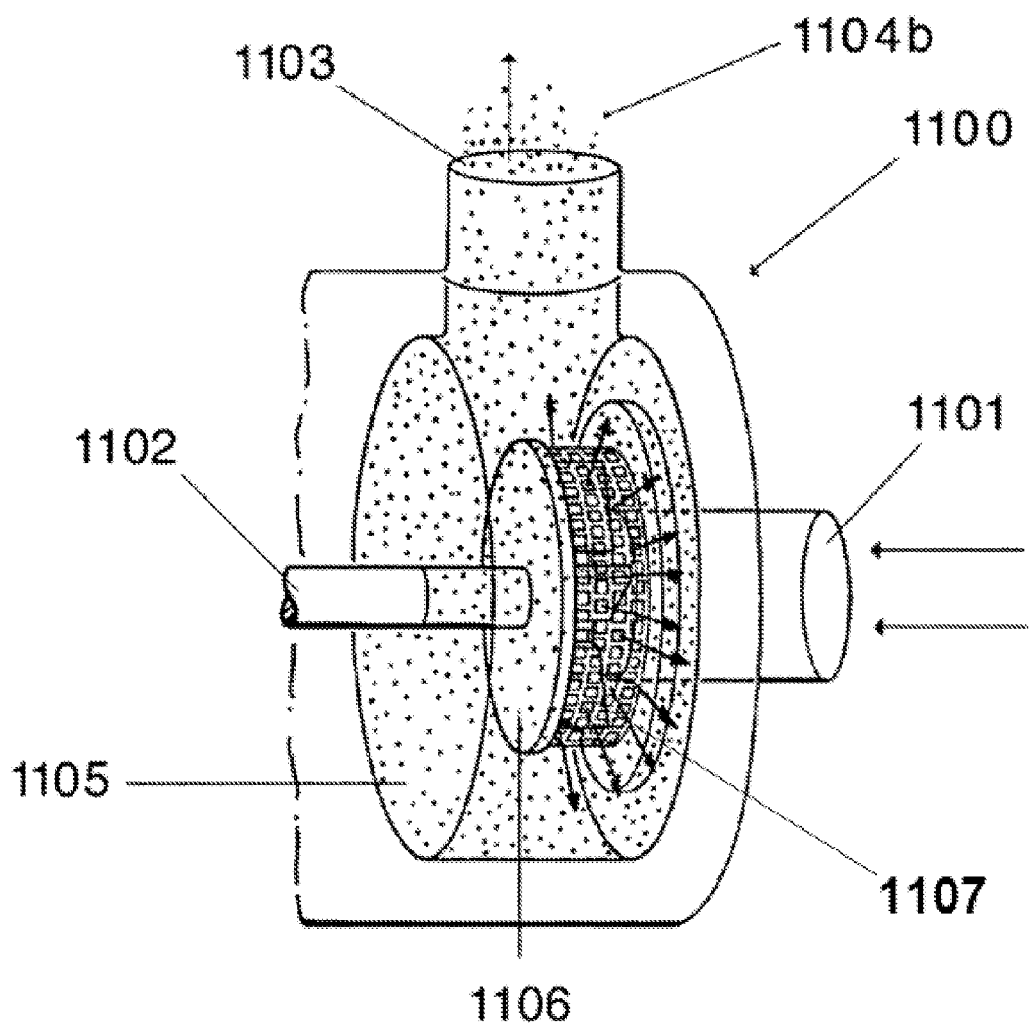

In one aspect, the mixing environment does not comprise a subsequent screen or a perforated stator such as the one shown in the mixing devices depicted in FIGS. 1A-C. Thus, in some aspects, the process stream is first screened, then enters a mixing environment, and is not screened or passed through a perforated stator in the mixing environment itself, in contrast to mixing environments created with rotor/stator type mixing devices, wherein a process stream enters the mixing environment without having been screened and then is propelled through a perforated stator through centrifugal force created by the rotor.

Once the emulsion or double-emulsion is formed, the solvent for the polymer (first solvent in single emulsion and second solvent in double-emulsion) is removed to provide the microparticles. Virtually any method known in the art for removing solvent to provide microparticles can be used. Suitable methods include, but are not limited to, spray drying, freeze drying, air drying, vacuum drying, fluidized-bed drying, milling, co-precipitation, solvent extraction, or a combination thereof. In the case of spray drying, freeze drying, air drying, vacuum drying, fluidized-bed drying and critical fluid extraction. In the case of milling, the components are mixed in the dried form and milled by any method known in the art. In the case of co-precipitation, the components are mixed in organic conditions and processed as described below. The components are mixed and dried using precision nozzles to produce extremely uniform droplets in a drying chamber. Suitable spray drying machines include, but are not limited to, Buchi, NIRO, APV and Lab-plant spray driers. Generally, the nature of the solvent-removal step will vary widely depending on whether or not the process is a batch process, continuous process, or a combination batch-continuous process and whether the process involves a single-emulsion or a double-emulsion. In one aspect, solvent removal is accomplished by extraction, evaporation, or a combination extraction and evaporation protocol, as discussed below.

In one aspect, the solvent can be removed by extraction followed by evaporation. According to this aspect, a portion of the first solvent is removed by extraction, and then evaporation is used to remove substantially all of the remaining solvent from the microdroplets or double-emulsion to provide the microparticles. Specifically, the process involves adding the emulsion or double-emulsion to an extraction phase to concentrate the dispersed phase or phases or to induce skin formation at the interface between the dispersed phase and continuous phase to form microspheres, preferably by injecting the emulsion or double-emulsion into a flowing stream of the extraction phase. The extraction phase generally comprises a non-solvent for the polymer and a solvent for the continuous phase components; and a limited solvent for the dispersed phase solvent. In one example, the dispersed phase solvent has a solubility of 0.1% to 25% by weight in the extraction phase. The process then involves further removing the first solvent from the microspheres using an evaporative process, preferably while the microspheres remain in the extraction phase. The formed microspheres can then be collected, washed, dried, and packaged using techniques known in the art. The process also can include using separation, or sizing, techniques known in the art for classifying microparticles by size.

According to this aspect, the purpose of performing extraction and evaporation sequentially is twofold. First, the process can control the rate of solvent removal from the dispersed phase droplets in such a manner that the surface and internal structure of the resulting microparticles provides the desired release properties. Second, the process can provide the desired microparticle properties while minimizing the amount of extraction phase needed and therefore the cost of the total process. In both stages of solvent removal, extraction and evaporation, solvent can be partition from the dispersed phase droplet or double-emulsion into the surrounding medium. The rate of partitioning is proportional to the concentration gradient of the dispersed phase solvent across the interface that exists between the dispersed phase and extraction phase solvent, and can therefore be controlled by controlling the concentration of the dispersed phase solvent in the extraction phase throughout the process. This can be controlled by adjusting the total volume of extraction phase, by further addition of extraction phase.

Control of the solvent removal rate can also be achieved by evaporating solvent from the extraction phase at a rate that is matched to the desired rate of solvent removal during the latter stage of the encapsulation process. In general, a slow rate of solvent removal will produce microparticles having a dense internal structure, while a fast rate of solvent removal will produce microparticles having a porous internal structure. The relationship between internal structure and the rate of solvent removal depends on factors such as the physicochemical properties of the agent, the polymer (composition and molecular weight), the dispersed phase solvent or solvents, and the concentration of agent and polymer in the dispersed phase.

The object of the extraction step of this aspect is to affect an initial rapid reduction in solvent in the dispersed phase to establish the desired skin and internal structure. Once the desired extent and rate of extraction needed for a particular formulation have been determined, the minimum amount of extraction phase needed to achieve the desired extent of extraction within the desired extraction time frame and under a given set of conditions can be determined empirically or calculated using known mathematical models. The object of the evaporation step is to maintain a relatively high driving force for partitioning of dispersed phase solvent, thereby minimizing the overall process time. The rate of evaporation needed to accomplish this objective can be determined by empirical methods or through the use of mathematical models. In a preferred aspect, between about 10% and about 90%, and more preferably between about 20% and 70%, of the solvent is removed by extraction.

According to this aspect, the evaporation step can be performed using techniques known in the art. Evaporation can be performed under atmospheric or reduced pressure conditions, and at ambient temperatures, or higher temperatures that do not harm the agent. An example of a continuous evaporation process is one in which the process stream exiting the extraction step is passed through a falling-film or wiped-film evaporator.

In another aspect, solvent removal can be performed using a continuous evaporation process. According to this aspect, the solvent is removed using only evaporation in a continuous process following a continuous emulsification process. No extraction is required, and consequently less process streams and process equipment are required than those including extraction.

According to this aspect, the dispersed phase or phases and continuous phase are prepared as described above. Following emulsification, the emulsion or double-emulsion is transferred directly to an evaporative process. In a preferred aspect, the emulsion flows into a large tank that is maintained under vacuum or reduced pressure, drawing off the solvent vapor. The tank may be heated, for example using an internal steam coil or external jacketing, in order to increase the rate of evaporation. The pressure and/or temperature selected depends on the solvent, polymer, and agent selected, as well as the relative amounts of these materials.

In yet another aspect, the solvent removal step can be performed using a solvent extraction by membrane separation method. According to this aspect, emulsification is followed first by extraction then by a membrane separation step to remove the remainder of the solvent after the skin-forming extraction step. For example, a semipermeable membrane selective for the dispersed phase solvent, an ultrafiltration membrane with an appropriate molecular weight cut-off, or a microfiltration membrane of suitable pore size can be used in place of a portion of pipe downstream from the point of injection of the extraction phase, i.e. the extraction lag tube.

According to this aspect, the rate of solvent removal is controlled by the properties of the membrane and the capacity of the fluid phase to hold the solvent. This solvent removal process preferably is performed on a continuous basis. The membrane separation process also provides fine control over the rate of solvent extraction, enabling one of skill in the art to create a microencapsulation process having a precise extraction profile, which, for example, can be computer controlled and adjusted during continuous operation, for instance, by adjusting the flow rate of the surrounding extraction fluid.

In yet another aspect, the solvent removal step can be performed using incremental extraction. According to this aspect, the solvent removal process involves introducing the extraction phase into the emulsion or double-emulsion through multiple feed streams rather than a single feed stream. The extraction phase is thereby combined with the emulsion at two or more locations along the extraction lag tube rather than in one location, preferably in a continuous process.

In this aspect, each incremental addition of extraction phase can be equal in its capacity to hold dispersed phase solvent, or the increments can differ. Furthermore, the position along the extraction lag tube at which the incremental additions are made can be controlled so that the extraction profile can be carefully programmed. With a sufficient number of extraction phase inlets, the extraction process effectively becomes a continuous process in which the rate of extraction is determined by the rate of addition of extraction phase, i.e. dilution of the emulsion.

In this aspect, the incremental extraction can be used to remove all the solvent to be removed from the microparticle, or a partial extraction process can be followed by an evaporation step to remove the solvent remaining after incremental extraction. The desired extent of extraction within the desired extraction time frame for a given set of conditions can be determined empirically or calculated using mathematical models.

In yet a further aspect, the solvent removal process can be performed using a two-phase solvent extraction. This solvent extraction process uses only two phases, rather than the typical three phases. The same phase is used both to form the emulsion or double-emulsion and to extract the solvent. This process requires less process equipment than a three phase continuous process for microencapsulation. While inherently simpler, the process requires careful control of the process variables, since there generally is only a narrow operating window at which the emulsion or double-emulsion is stable enough to form spherical disperse phase droplets before extraction precipitates the polymer.

According to this aspect, there are two primary process conditions that can be used in the extraction. The first condition is to operate at saturation levels of solvent, producing a solvent evaporation condition, rather than solvent extraction. The solvent is removed from a quench tank, possibly using a vacuum assist. The second condition is to operate at below solvent saturation levels, producing a solvent extraction condition. Process variables for this condition, however, must be carefully adjusted to provide a metastable emulsion or double-emulsion, in order to form dispersed phase droplets having desired diameters and surface characteristics.

When the first solvent is removed using extraction, for example, using any of the extraction procedures described above, the extraction phase generally comprises a solvent for the continuous phase components, a limited solvent for the dispersed phase solvent, and a nonsolvent for the polymer. The first solvent (or the first solvent component of greatest proportion if a mixture of solvents are used for the first solvent) should generally have a solubility in the extraction phase of from about 0.1% and 25% by weight. When water insoluble polymers are used, the extraction phase preferably is deionized water. The extraction phase can contain buffers to limit agent solubility in the extraction phase.

Any of the common buffers, such as phosphate, acetate, or tris, are suitable for use with the extraction phase, provided that they are compatible with the surfactant system chosen. Salts can also be used, such as sodium chloride, potassium chloride, and the like. When making microparticles for pharmaceutical or biomedical applications, the buffer also should be pharmaceutically acceptable. The buffering system should be selected to provide a pH in the extraction phase which provides minimum solubility of the active agent.

In a further aspect, solvent removal can be performed entirely or partially using a cryogenic extraction step. This is a process in which a cold extraction medium is used to freeze the polymer, the solvent for the polymer, or both in the emulsion or double-emulsion. The cryogenic process provides an enhanced ability to control the mobility of the agent, keeping it in the microparticle based on the appropriate selection of solvent and temperatures. The lower temperatures also can stabilize the agent, particularly bioactive agents.

The selection of the solvent for the dispersed phase, which includes the third solvent in the case of a double-emulsion process, used in the process generally depends on the polymer and agent chosen, as well as the particular means of solvent removal to be employed. More than one solvent can be used in the dispersed phase, including for example, the first and third solvent, which can be the same or different. Organic solvents, such as acetone, methyl ethyl ketone, ethyl lactate, ethyl acetate, dichloromethane, and ethyl acetate/alcohol blends, are preferred for use with polyesters such as poly(lactide), poly(glycolide), poly(lactide-co-glycolide), poly(caprolactone), or combinations thereof, and cellulose ethers, cellulose esters, and acrylics. For other polymers, such as polyethylene glycol, poly(vinyl alcohol), and carboxymethylcellulose, water can be preferred as the first solvent.

The polymer of the dispersed phase can be a wide variety of different polymers. The polymers can be homopolymers or copolymers, including block or blocky co- or ter-polymers, random co- or ter-polymers, star polymers, or dendrimers. Any desired molecular weight polymer can be used, depending on the desired properties of the microparticle. If a high strength polymer is desired, then high molecular weight polymers can be used, for example, to meet strength requirements. In other aspects, low or medium molecular weight polymers can be used when, for example, when resorption time of the polymer, rather than microparticle strength is desired. Preferably, polymers used in the process are both biocompatible and biodegradable.

The molecular weight of the polymer can be important for degradable microparticles given that molecular weight influences the degradation rate of the polymer. For a diffusional mechanism of release, the polymer should remain intact until all of the agent is released from the polymer and then degrade. The agent can also be released from the polymer as the polymer erodes. By an appropriate selection of polymeric materials, a polymer formulation can be made such that the resulting polymer exhibits both diffusional release and degradation release properties. Molecular weights can be measured by methods known in the art, including gel permeation chromatography, viscosity, light-scattering, among other methods.

The polymer can be formulated so as to degrade within a desired time interval, once present in a particularly medium. In some aspects, the time interval can be from about less than one day to about 1 month. Longer time intervals can extend to 6 months, including for example, polymers that degrade from about ≥0 to about 6 months, or from about 1 to about 6 months. In other aspects, the polymer can degrade in longer time intervals, up to 2 years or longer, including, for example, from about ≥0 to about 2 years, or from about 1 month to about 2 years. A sustained release formulation of the microparticle and agent can release the agent over any of these time periods and under a wide variety of release profiles.

The desired agent release mechanism can influence the selection of the polymer. A biocompatible polymer, for example, can be selected so as to release or allow the release of a agent therefrom at a desired lapsed time after the microparticle has been administered to a subject. For example, the polymer can be selected to release or allow the release of the agent prior to the agent beginning to diminish its activity, as the agent begins to diminish in activity, when the agent is partially diminished in activity, for example at least 25%, at least 50% or at least 75% diminished, when the agent is substantially diminished in activity, or when the agent is completely gone or no longer has activity.

Specific examples of suitable polymers include one or more of a poly(lactide), a poly(glycolide), a poly(lactide-co-glycolide), a poly(caprolactone), a poly(orthoester), a poly(phosphazene), a poly(hydroxybutyrate) or a copolymer containing a poly(hydroxybutyrate), a poly(lactide-co-caprolactone), a polycarbonate, a polyesteramide, a polyanhydride, a poly(dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

Lactide-based polymers can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly(D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

In a particular aspect, when the biodegradable polymer is poly(lactide-co-glycolide), or a mixture of poly(lactide) and poly(glycolide), the amount of lactide and glycolide in the polymer can vary. In a further aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios. Similarly, a poly(lactide-co-caprolactone) can be 0: 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % caprolactone.

The processes disclosed herein can be used to form microparticles from a variety of materials, and in some aspects biocompatible and biodegradable materials. "Biodegradable," as defined herein, means the polymer will degrade or erode in vivo to form smaller chemical species, wherein the degradation can result, for example, from enzymatic, chemical, and physical processes. The term "biocompatible" is used herein to refer to a polymer and any degradation products of the polymer that are non-toxic to a recipient and present no significant deleterious effects on the recipient's body. Examples of suitable biocompatible, biodegradable polymers include many of those discussed above, such as polyesters (polyhydroxy acids), such as poly(lactide)s, poly(glycolide)s, poly(lactide-co-glycolide)s, poly(lactic acid)s, poly(glycolic acid)s, poly(lactic acid-co-glycolic acid)s, poly(lactide-co-caprolactone)s, poly(lactide-co-glycolide-caprolactone)s, polyanhydrides, polyorthoesters, polyetheresters, polycaprolactone, polyesteramides, polyphosphazines, polycarbonates, polyamides, and copolymers and blends thereof. Biocompatible, non-biodegradable polymers suitable for use in the processes described herein include polyacrylates, ethylene-vinyl acetate copolymers, modified celluloses such as cellulose ethers and cellulose esters, non-degradable polyurethanes, polystyrenes, polyvinyl chloride, polyvinyl fluoride, poly(vinyl alcohol), poly(vinyl imidazole), chlorosulphonate polyolefins, polyethylene oxide, and copolymers and blends thereof. Specific examples of such polymers are discussed above.

Virtually any agent which can be released from a microparticle can be used with the invention. The agent can be a bioactive agent or non-bioactive agent. Examples of non-bioactive agents that can be encapsulated by this method include, but are not limited to, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellents, solvents, stabilizers, polymer additives, and the like.

Likewise, various types of bioactive agents can be used, which are capable of being released from polymer into a medium, for example a subject. As used herein, a "bioactive agent" refers to an agent that has biological activity. In some aspects, the biological agent can be used to treat, diagnose, cure, mitigate, prevent (i.e., prophylactically), ameliorate, modulate, or have an otherwise favorable effect on a disease, disorder, or infection that is present in a subject. A liquid or solid bioactive agent can be used. The bioactive agents can be water soluble or water-insoluble, depending on the nature of the disclosed process. In some aspects, the bioactive agent is at least very slightly water soluble, and preferably moderately water soluble. The bioactive agents can include salts of the active ingredient. As such, the bioactive agents can be acidic, basic, or amphoteric salts. They can be nonionic molecules, polar molecules, or molecular complexes capable of hydrogen bonding. The bioactive agent can be included in the compositions in the form of, for example, an uncharged molecule, a molecular complex, a salt, an ether, an ester, an amide, polymer drug conjugate, or other form to provide the effective biological or physiological activity.

Examples of bioactive agents that can be used include, but are not limited to, small molecules, peptides, proteins such as hormones, enzymes, antibodies, antibody fragments, antibody conjugates, nucleic acids such as aptamers, iRNA, siRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents. Bioactive agents contemplated for use in the disclosed compositions include anabolic agents, antacids, anti-asthmatic agents, anti-cholesterolemic and anti-lipid agents, anti-coagulants, anticonvulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestyramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Still other bioactive agents include, but are not limited to, peptide drugs, protein drugs, therapeutic antibodies, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent can further be a substance capable of acting as a stimulant, sedative, hypnotic, analgesic, anticonvulsant, and the like.

Still other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin B12, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythropoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Timidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

The microparticles prepared by the disclosed process can be used in a variety of applications, such as cosmetics, agriculture, pharmaceuticals, among others. In one specific aspect, the microparticles can be used in pharmaceutical compositions. For pharmaceutical compositions, the agent will generally be a bioactive agent, but does not have to be. For example, the releasable agent can be a non-bioactive substance and still be used in a pharmaceutical composition. A variety of pharmaceutical compositions comprising the microparticle can be conveniently prepared in a desired dosage form, including, for example, a unit dosage form or controlled release dosage form, and prepared by any of the methods well known in the art of pharmacy. In general, pharmaceutical compositions are prepared by uniformly and intimately bringing the microparticle into association with a carrier or a finely divided solid carrier, or both, if necessary. In some aspects, the microparticle itself can be the carrier and/or can be combined with other carriers or additives. Other pharmaceutical carriers can also be used. Examples of solid carriers, other than the polymer (if solid), include lactose, terra alba, sucrose, talc, gelatin, agar, pectin, acacia, magnesium stearate, and stearic acid. Examples of liquid carriers, other than the polymer (if liquid), are sugar syrup, peanut oil, olive oil, and water. Examples of gaseous carriers include carbon dioxide and nitrogen. Other pharmaceutically acceptable carriers or components that can be mixed with the bioactive agent can include, for example, a fatty acid, a sugar, or a salt.

The continuous phase at least comprises a solvent that is either partially or totally immiscible with the solvent used in the dispersed phase. Generally, the solvent for the continuous phase is aqueous when the dispersed phase is organic, and the continuous phase is non-aqueous when the dispersed phase is aqueous. Thus, the emulsion can be an oil-in-water emulsion or a water-in-oil emulsion. Likewise, the double-emulsion can comprise either a water-in-oil-in-water double emulsion or a oil-in-water-in-oil double emulsion.

The continuous phase can in some aspects be aqueous and can further comprise at least one surfactant or emulsifying agent. Polyvinyl alcohol (PVA) is a preferred surfactant when water is used as the continuous phase solvent. Other emulsifiers or surfactants which can be used include many emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and co-polymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di-, and tri-glycerides of saturated or unsaturated fatty acids, glycerides or soya-oil and sucrose. Other emulsifiers include natural and synthetic forms of bile salts or bile acids, both conjugated with amino acids and unconjugated such as taurodeoxycholate, and cholic acid.

When the continuous phase comprises a surfactant, the surfactant should be present in a concentration sufficient to form a stable emulsion with the dispersed phase using the mixing means selected. For example, if the process relies on low-intensity emulsification, such as emulsion lag tube turbulence (described below), then enough surfactant must be present to lower the surface tension of the continuous phase. Preferably, the surfactant should constitute from about 0.1 and 20% by weight of the continuous phase.

The continuous phase also preferably includes dispersed phase solvent, which reduces or eliminates partitioning of the solvent from the dispersed phase into the continuous phase during emulsification. The amount of dispersed phase solvent added to the continuous phase may vary depending on the specific polymer/agent combination used. Generally, the amount of dispersed phase solvent is between about 5% and 100% of the amount needed to saturate the continuous phase, for example about 7.5%. As discussed above, the continuous phase, like the extraction phase, can optionally further comprise buffers or salts, as discussed above. The continuous phase can further be manipulated by an adjustment of pH of the phase.

Figure 2A:
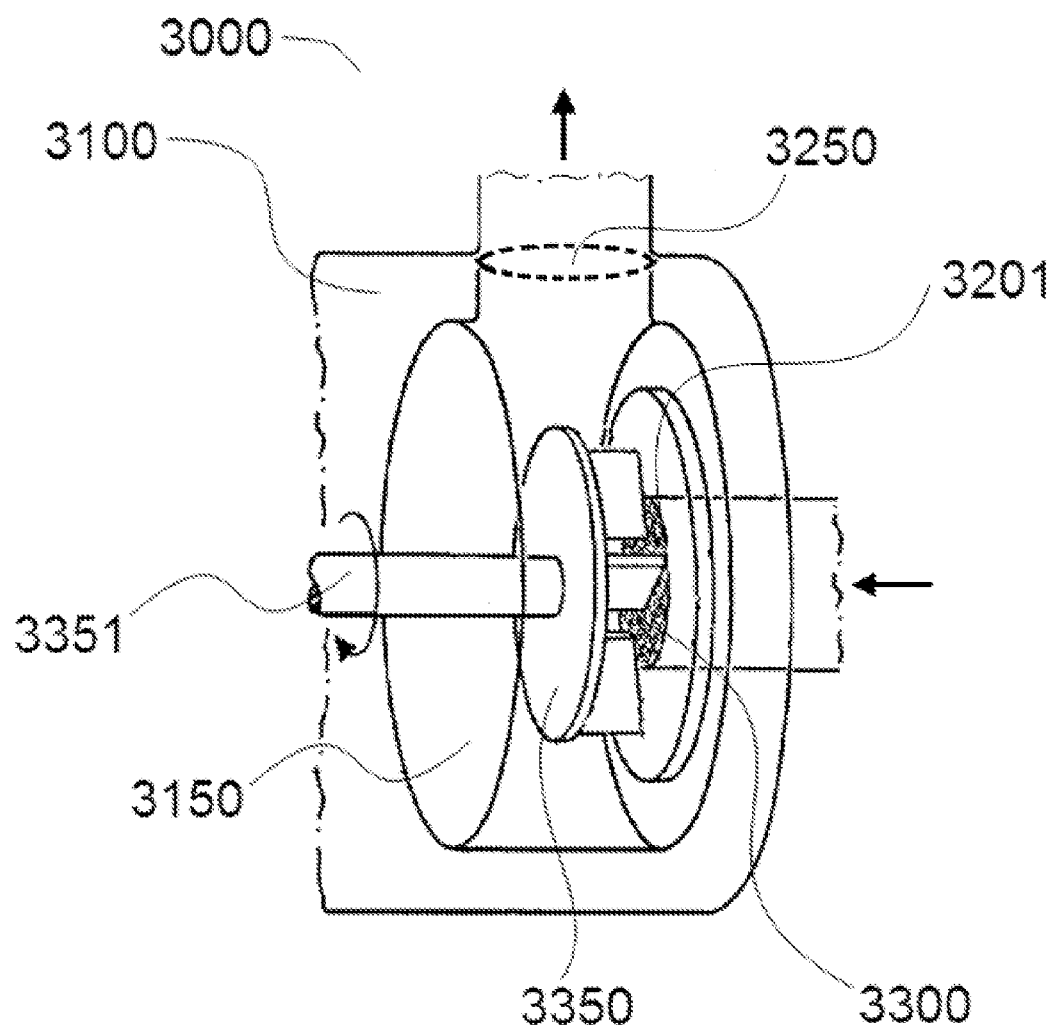
FIG. 2A is a drawing of an exemplary workhead assembly according to the present invention.

The invention also relates to workhead assemblies which can be used in non-static flow-through mixers, for example, to mix two or more streams of fluids and/or solids, and can be used with the process of the invention. With reference to FIG. 2A, a preferred workhead assembly 3000 for a non-static flow through mixer comprises a housing 3100 forming a mixing chamber 3150 and defining a fluid inlet port 3201 in communication with the mixing chamber 3150 and a fluid outlet port 3250 in communication with the mixing chamber 3150. The workhead assembly 3100 comprises a screen mesh 3300 extending across the inlet port 3201. As fluid enters to fluid inlet port 3201, it will first pass through the screen 3300 which extends across the fluid inlet port 3201 prior to entering into the mixing chamber 3150. In the mixing chamber 3150 there is a rotor 3350 positioned within the housing 3100 and between the screen 3350 and the fluid outlet port 3250 such that when the rotor 3350 is rotated, fluid is directed from the inlet port 3201, through the screen mesh 3300, to the outlet port 3250. As shown in FIG. 2A, and in contrast to the devices shown in FIGS. 1A-C, the workhead does not have a perforated stator or a screen positioned in the mixing chamber itself, after the rotor, or a screen positioned between the rotor and the fluid outlet port.

The screen mesh 3300 can be made from any desirable material, as discussed above, but is preferably a material that will not corrode when it encounters the incoming fluid. Thus, a variety of types of materials can be used in the screen but generally will be limited by the particular mixing process. The screen of the workhead can comprise any of those materials discussed above in reference to the screening step of the process.

The porosity of the screen can vary widely depending on the mixing process in which the workhead assembly is used. For example, when the workhead assembly is being used to mix the continuous and dispersed phases of the disclosed process, the screen preferably has a porosity of from about 0.1 to about 1000 µm, and more preferably from about 10 to about 500 µm. In specific examples wherein the workhead assembly is used with the disclosed process, the screen has a porosity of about 125 µm or about 75 µm.

In operation, referring again to FIG. 2A, as fluid enters the fluid inlet port 3201, and passes through the screen 3300 extending across the inlet port 3201, it encounters the spinning rotor 3350 which will generally have rotor blades. The rotor 3350 functions to create suction through the inlet port 3201, mixes the fluid, and drives the fluid toward the exit port 3250. The rotor can comprise a rotatable shaft 3351 for rotating the rotor at a desired speed. Such a rotor 3350 can generally operate at a high number of revolutions per minute depending on the source that drives the rotor. For example, when the workhead assembly is used with the disclosed process, rotor 3350 speeds can generally range from about 10 revolutions per minute (RPM) to about 12,000 RPM, and preferably are from about 500 RPM to about 1200 RPM. The spinning rotor 3350 creates what is referred above as a mixing environment.

Figure 2B:
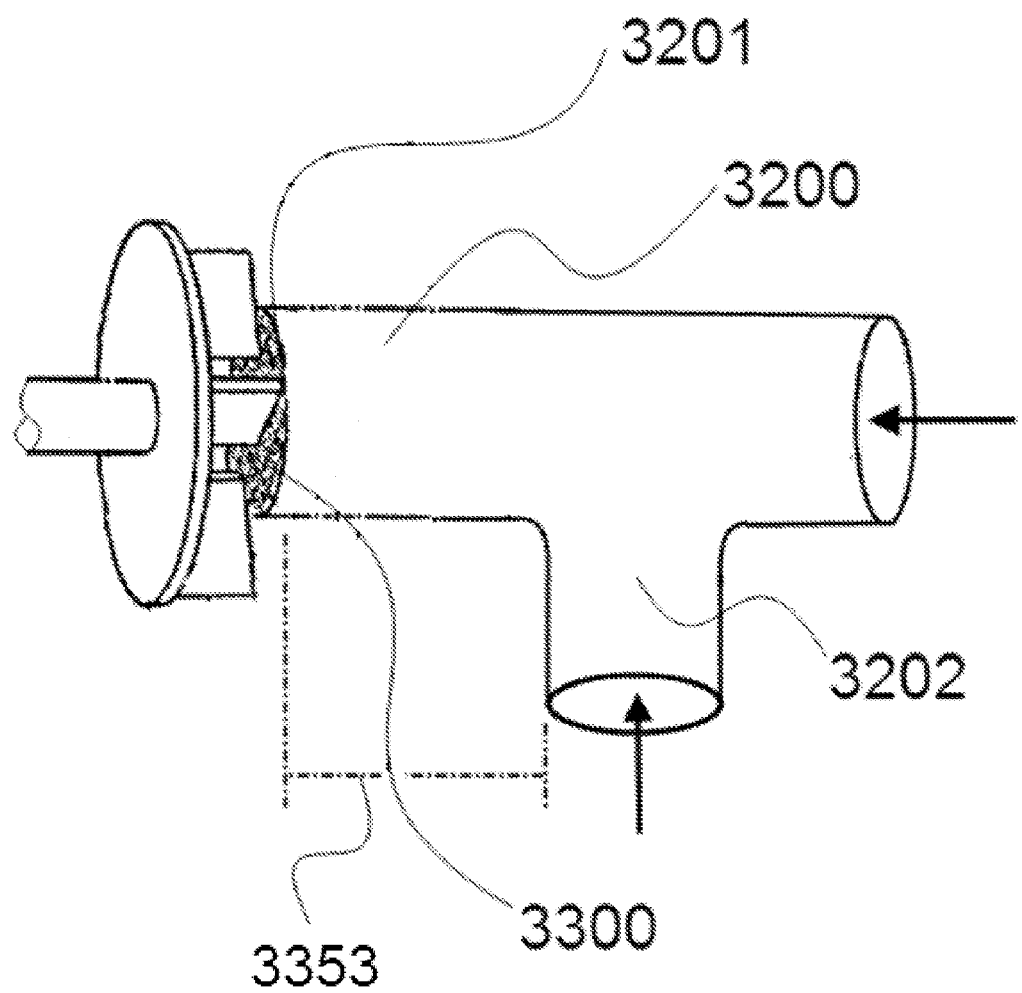
FIG. 2B is a drawing of a portion of the workhead, which is connected to an inlet pipe.

The fluid inlet 3201 and outlet ports 3250 can be connected to piping which can contain the fluid flowing into and out of the mixing chamber 3150 and which can connect the mixing step to another step in a particular process. Referring now to FIG. 2B, the fluid inlet port 3201 can be in communication with a fluid inlet pipe 3200. The fluid inlet pipe 3200 can be split into or comprise one or more other pipes which can contain other process fluid. For example, with reference to FIG. 2B, in communication with main inlet pipe 3200 there is a side inlet pipe 3202. Depending on the process, the location of the side inlet pipe 3202 can be important, inasmuch as the location of side inlet pipe 3202 affects when and how two or more fluids will be combined with the fluid flowing through the main inlet pipe 3200. For example, when the workhead assembly is being used in a microencapsulation process, such as the disclosed process, the side inlet pipe can be positioned at a distance 3353 ranging from about 0 to about 20 cm, preferably from about 0 to about 5.5 cm, and more preferably from about 0 to about 0.6 cm, including for example, 0.32 cm and 0.64 cm.

Figure 2C:
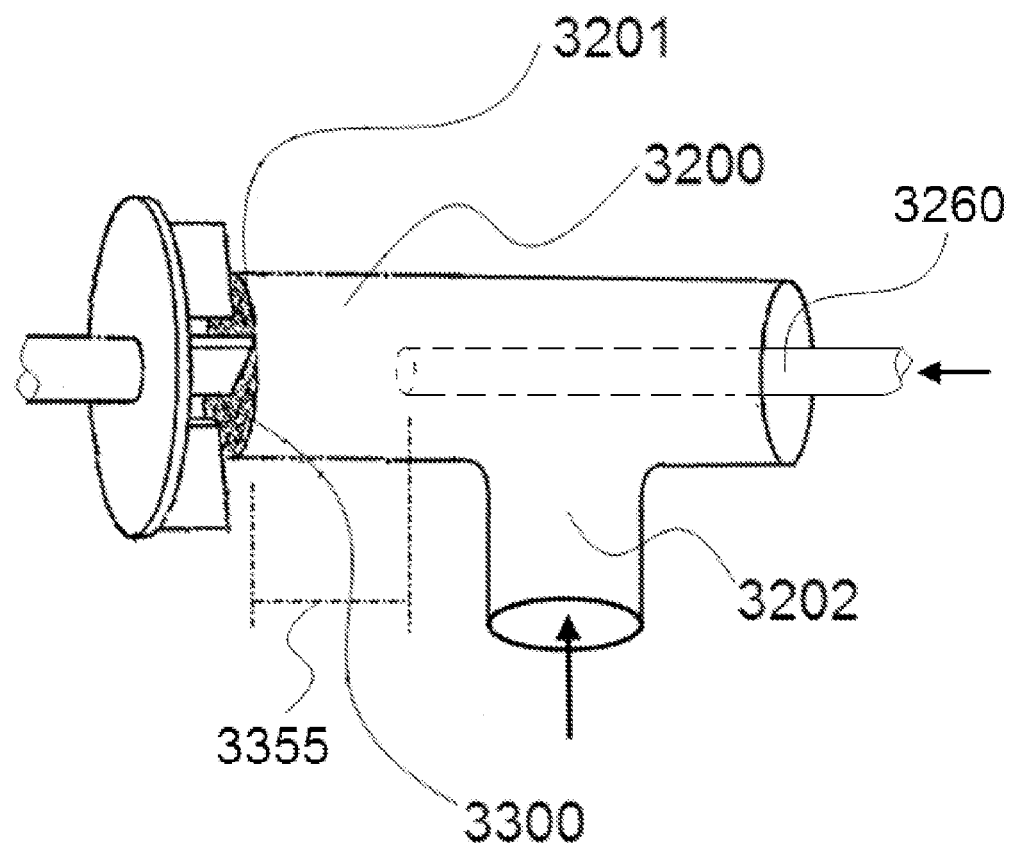
FIG. 2C is a drawing of an alternate embodiment of a portion of the workhead, which is connected to an inlet pipe configured as a tube-in-tube.

Referring now to FIG. 2C, the fluid inlet port 3201 can be in communication with a fluid inlet pipe 3200 and also in communication with an inner inlet pipe 3260 through which a fluid such as the dispersed phase can be introduced. The inner inlet pipe 3260 is positioned within the outer fluid inlet pipe 3200. The inner pipe 3260 can be secured to the outer pipe through any appropriate means, such as through struts holding the inner pipe within the outer pipe. In this embodiment, the inner inlet pipe 3260 can be positioned a distance 3355 away from the screen. This distance can generally range from 0 to 20 cm, preferably from about 0 to about 5.5 cm, and more preferably from about 0 to about 0.6 cm, including for example, 0.32 cm and 0.64 cm. The distance 3355 can be changed by sliding the inner pipe 3260 closer to or away from the screen. The position of the inner tube, like the position of the side-inlet tube will generally affect the point at which two fluids, such as a dispersed phase and a continuous phase, are mixed and can therefore be adjusted appropriately.

With reference to the disclosed process and FIGS. 2A-2C, the dispersed phase can be flowed through the main inlet pipe 3200 (or inner tube 3260), while the continuous phase can be flowed through side inlet pipe 3202. As the continuous phase flows through side inlet pipe 3202 (or inner tube 3260), the dispersed phase (or the primary emulsion) and the continuous phase are combined, although not necessarily mixed. The combined phases are referred to above as the process stream. The process stream then passes into inlet port 3201 and through the screen 3300, which can help the formation of microdroplets in the emulsion. The process stream then encounters the rotor 3350. and is mixed in the mixing environment created by the rotor 3350. The emulsion or double-emulsion is then forced through the fluid outlet port 3250 and continues along in the microencapsulation process. In some aspects, the next step according to the disclosed process will be the extraction or drying step wherein solvent is partially or completely removed from the microdroplets or double-emulsion to thereby provide the microparticles.

The workhead assembly can be made according to any desired method. In a preferred aspect, the workhead assembly is made by modifying a conventional or commercially available workhead of a flow-through mixing device, such as a SILVERSON mixer. The modification involves removing the stator from the workhead (e.g., element 1107 in FIGS. 1A-C) and installing the screen across the fluid inlet port.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Particle size analysis was performed by laser-diffraction and the reported sizes are based on volume-averaged statistics Example 1

Preparation of a Workhead Assembly

A workhead assembly for a non-static flow through mixer was prepared by modifying a commercially available SILVERSON L4R-TA in-line mixer head (SILVERSON Machines Inc., East Longmeadow, Mass., U.S.A.) in the following manner. The stator was removed from the SILVERSON L4R-TA in-line mixer head and a screen having a 75 µm or 125 µm pore size was placed at the opening of the intake (inlet) port on the bottom plate of the mixer head. The stator (e.g., component 1107 in FIG. 1A) was removed from the mixer head. An injection tube for the dispersed phase was placed before the screen. The injection tube was placed before the screen such that the distance between the injection tube and the screen was either between 0 inches and 0.125 inches or about 0.25 inches. These distances were measured from the side of the screen closest to the injection tube to the tip of the injection tube closest to the screen. The tube diameter for the dispersed phase was either 0.125 inches or 0.25 inches. An injection tube for the continuous phase was place in-line with the inlet port of the workhead assembly.

Example 2

Placebo Microparticles Prepared Using 125 µm Screen

Microparticle batches were prepared in a process using the workhead assemblies with a 125 µm screen as described in Example 1. The average dispersed phase (DP) flow-rate was about 25 g/min and the average continuous phase (CP) flow-rate was about 200 g/min, so that the total flow rate through the screen (DP+CP rate, g/min) was about 225 g/min. Where indicated, the total flow rate (DP+CP rate) was lowered to either 75% of initial (to about 170 g/min) or 50% of initial (to about 112 g/min) while maintaining a fixed ratio of the CP flow rate to the DP flow rate. The average extraction phase flow-rate was about 1500 g/min. Polymer concentration in the dispersed phase for all batches was 20% in ethyl acetate. The polymer used was poly(D,L-lactide) having an intrinsic viscosity (IV) of about 0.36 dL/g. The continuous phase was a 2 weight % polyvinyl alcohol (PVA) solution saturated at 7.5% ethyl acetate. Particle size data shown in Table 1 were taken from a hardening bath. The microparticles were collected on a 20 µm screen, and then freeze-dried. Yields are based on initial input of polymer and the weight of the microparticles collected after sieving on a 20 micron screen and freeze drying. A 125 µm scalping screen was not used. Table 1 shows the results. These microparticles were "placebo" microparticles and did not contain an agent. The breadth of a particle size distribution was characterized using not only the parameter $D_{50}$, for which 50% of the particles are greater than or smaller than the value $D_{50}$, but also $D_{10}$, which designates the particle size for which 10% of the particles are smaller than $D_{10}$. Likewise, $D_{90}$ designates the particle size for which 90% of the particles are smaller than the value $D_{90}$. The breadth of the particle size distribution can be characterized by the following formula: Breadth=$(D_{90}-D_{10})/D_{50}$. The smaller the breadth value, the narrower the particle size distribution.

TABLE 1

| Lot # | Screen size (µm) | Workhead speed (RPM) | $D_{10}$ (µm) | $D_{50}$ (µm) | $D_{90}$ (µm) | $D_{90}/D_{10}$ | Breadth | DP + CP flow | Batch size (g) | Yield (%) |
|---|---|---|---|---|---|---|---|---|---|---|
| 00210-116 | 125 | 1200 | 22 | 62 | 109 | 4.9 | 1.40 | 225 | 10 | 73 |
| 00210-138 | 125 | 900 | 39 | 79 | 120 | 3.1 | 1.03 | 225 | 20 | 91.5 |
| 00210-119 | 125 | 500 | 74 | 113 | 153 | 2.1 | 0.70 | 225 | 10 | 69 |
| 00210-150 | 125 | 0 | 174 | 464 | 890 | 5.1 | 1.54 | 225 | 20 | 64 |
| 00210-141 | 125 | 1200 | 36 | 83 | 127 | 3.5 | 1.10 | 170 | 20 | 91 |
| 00210-144 | 125 | 900 | 53 | 87 | 122 | 2.3 | 0.79 | 112 | 20 | 92.5 |

Figure 3:
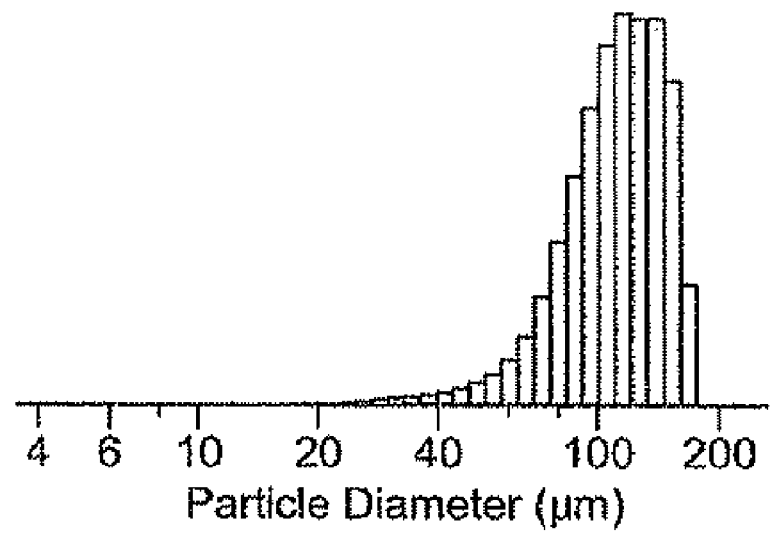
FIG. 3 is a plot of particle diameter distribution derived from data obtained from a microparticle batch of Example 2 described below.

A plot of particle diameter distribution derived from data obtained from Lot #00210-119-00 is shown in FIG. 3.

Example 3

Placebo Microparticles Prepared Using 75 µm Screen

Microparticle batches were prepared in a process using the workhead assemblies with a 75 µm screen as described in Example 1. The average dispersed phase (DP) flow-rate was about 25 g/min. The average continuous phase (CP) flow-rate was about 200 g/min, and the average dispersed phase (DP) flow rate was 25 g/min. Where indicated, the total flow rate (DP+CP rate) was lowered to either 75% of initial (to about 170 g/min) or 50% of initial (to about 112 g/min) while maintaining a fixed ratio of the CP flow rate to the DP flow rate. The average extraction phase flow-rate was about 1500 g/min. Polymer concentration in the dispersed phase for all batches was 20% in ethyl acetate. The polymer used was poly(D,L-lactide) having an intrinsic viscosity (IV) of about 0.36 dL/g. The continuous phase was a 2 weight % polyvinyl alcohol (PVA) solution saturated at 7.5% ethyl acetate. Particle size data shown in Table 2 were taken from a hardening bath. The microparticles were collected on a 20 µm screen, and then freeze-dried. Yields are based on initial input of polymer and the weight of the microparticles collected after sieving on a 20 micron screen and freeze drying. A 125 µm scalping screen was not used. Table 2 shows the results. These microparticles were "placebo" microparticles and did not contain an active agent.

TABLE 2

| Lot # | Screen size (μm) | Workhead speed (RPM) | $D_{10}$ (μm) | $D_{50}$ (μm) | $D_{90}$ (μm) | $D_{90}/D_{10}$ | Breadth | DP + CP flow | Batch size (g) | Yield (%) |
|---|---|---|---|---|---|---|---|---|---|---|
| 00210-123 | 75 | 1200 | 10 | 40 | 66 | 6.6 | 1.40 | 225 | 20 | 88 |
| 00210-129 | 75 | 900 | 32 | 88 | 136 | 4.2 | 1.18 | 225 | 20 | 91 |
| 00210-125 | 75 | 500 | 30 | 75 | 118 | 3.9 | 1.17 | 225 | 10 | 91 |
| 00210-132 | 75 | 1200 | 24 | 39 | 56 | 2.3 | 0.82 | 170 | 20 | 86 |
| 00210-135 | 75 | 900 | 27 | 48 | 74 | 2.7 | 0.98 | 112 | 20 | 83 |

Example 4

Comparative Placebo Microparticles Prepared Using Rotor/Stator Workhead to a Screen/Rotor Workhead (Lot 00277-039)

Microparticle batches were prepared in a process using a standard rotor/stator workhead assembly on a commercially available SILVERSON L4R-TA in-line mixer as discussed in Example 1 (unmodified SILVERSON L4R-TA). The average dispersed phase (DP) flow-rate was about 50 g/min, and the average continuous phase (CP) flow rate was about 250 g/min. The average extraction phase flow-rate was about 1500 g/min. Polymer concentration in the dispersed phase for all batches was 20% in ethyl acetate. The polymer used was poly(D,L-lactide) having an intrinsic viscosity (IV) of about 0.36 dL/g. The continuous phase was a 2 weight % polyvinyl alcohol (PVA) solution saturated at 7.5% ethyl acetate. Particle size data shown in Table 3 were taken from a hardening bath. The microparticles were collected on a 20 μm screen, and then freeze-dried. Yields are based on initial input of polymer and the weight of the microparticles collected after sieving on a 20 micron screen and freeze drying. A 125 μm scalping screen was not used. Table 3 shows the results. These microparticles were "placebo" microparticles and did not contain an active agent. For comparison, "placebo" microparticles were made by a method of the present invention using a 125 micron screen and a rotor speed of 500 rpm. The DP flow rate was about 50 g/min, the CP flow rate was about 250 g/min, and the EP flow rate was about 2500 g/min (lot 00277-039-00).

TABLE 3

| Lot # | SILVERSON speed (RPM) | $D_{10}$ (μm) | $D_{50}$ (μm) | $D_{90}$ (μm) | $D_{90}/D_{10}$ | Batch size (g) | Yield (%) |
|---|---|---|---|---|---|---|---|
| 00277-039-00 | NA, 500 and 125 micron screen | 30 | 65 | 110 | 3.7 | 20 | 90 |
| 00277-090-00 | 1200 | 16 | 43 | 73 | 4.6 | 20 | 50 |
| 00277-093-00 | 900 | 43 | 80 | 122 | 2.8 | 20 | 72 |
| 00277-096-00 | 500 | 49 | 101 | 142 | 2.9 | 20 | 75 |

Figure 4:
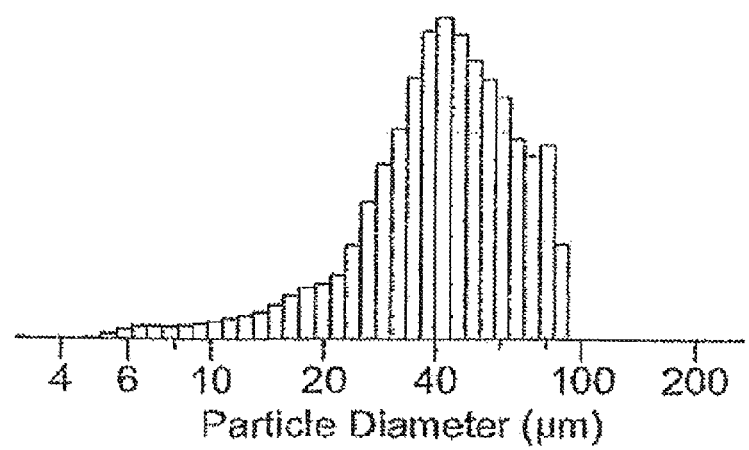
FIG. 4 is a plot of particle diameter distribution derived from data obtained from a microparticle batch of Example 4 described below.

A plot of particle diameter distribution derived from data obtained from Lot #00277-090-00 is shown in FIG. 4.

Example 5

Goserelin-Loaded Microparticles Prepared Using a 125 μm Screen

Goserelin-loaded microparticle batches were prepared in a process using the workhead assemblies with a 125 μm screen as described in Example 1. The theoretical Goserelin loading was 10 weight %, and the actual Goserelin loading was 4.2%. The average dispersed phase (DP) flow-rate was about 25 g/min. The average continuous phase (CP) flow-rate was about 200 g/min. The average extraction phase flow-rate was about 1500 g/min. Polymer concentration in the dispersed phase for all batches was 20% in ethyl acetate. The polymer used was poly(D,L-lactide) having an intrinsic viscosity (IV) of about 0.36 dL/g. The continuous phase was a 2 weight % polyvinyl alcohol (PVA) solution saturated at 7.5% ethyl acetate. Particle size data were taken from a hardening bath. The microparticles were collected on a 20 μm screen, and then freeze-dried. Yields are based on initial input of polymer and the weight of the microparticles collected after sieving on a 20 micron screen and freeze drying. A 125 μm scalping screen was not used. Table 4 shows the results.

TABLE 4

| Lot # | Screen size (μm) | Workhead speed (RPM) | $D_{10}$ (μm) | $D_{50}$ (μm) | $D_{90}$ (μm) | $D_{90}/D_{10}$ | Breadth | Batch size (g) | Yield (%) |
|---|---|---|---|---|---|---|---|---|---|
| 00210-147 | 125 | 900 | 36.9 | 68.8 | 100.8 | 2.73 | 0.93 | 10 | 88 |

Example 6

Naltrexone-Loaded Microparticles Prepared Using a 125 μm Screen

Naltrexone-loaded microparticle batches were prepared in a process using the workhead assemblies with a 125 μm screen as described in Example 1. Naltrexone theoretical loading was 25 weight %, and the actual Naltrexone loading was 20 weight %. The average dispersed phase (DP) flow-rate was about 52 g/min. The average continuous phase (CP) flow-rate was about 249 g/min. The average extraction phase flow-rate was about 2500 g/min. Polymer concentration in the dispersed phase was 20% in ethyl acetate. The polymer used was poly(D,L-lactide) having an intrinsic viscosity (IV) of about 0.36 dL/g. The continuous phase was a 2 weight % polyvinyl alcohol (PVA) solution saturated at 7.5% ethyl acetate. Particle size data were taken from a hardening bath. The microparticles were collected on a 20 μm screen, and then freeze-dried. Yields are based on initial input of polymer and the weight of the microparticles collected after sieving on a 20 micron screen and freeze drying. A 125 μm scalping screen was not used. Table 5 shows the results.

TABLE 5

| Batch | Workhead speed (RPM) | $D_{10}$ (μm) | $D_{50}$ (μm) | $D_{90}$ (μm) | $D_{90}/D_{10}$ | Breadth | Batch size (g) | Yield (%) |
|---|---|---|---|---|---|---|---|---|
| Naltrexone-loaded (Lot 00277-044) | 500 | 43 | 78 | 125 | 2.91 | 1.05 | 25 | 85 |

TABLE 6

Process parameters

| Lot # | CP Flow rate (g/min) | CP/DP | Workhead speed (RPM) | DP Tube diameter (inches) | DP Tube position |
|---|---|---|---|---|---|
| 00339-006 | 125 | 10 | 800 | 0.25 | 0.25 |
| 00339-009 | 200 | 10 | 1200 | 0.25 | 0.25 |
| 00339-015 | 125 | 5 | 800 | 0.125 | 0.25 |
| 00300-140 | 200 | 10 | 800 | 0.125 | 0 |
| 00339-040 | 200 | 5 | 800 | 0.25 | 0 |
| 00339-027v | 200 | 5 | 1200 | 0.125 | 0.25 |
| 00339-033 | 125 | 5 | 1200 | 0.25 | 0 |
| 00300-143 | 125 | 10 | 1200 | 0.125 | 0 |

TABLE 7

Results obtained from process using parameters listed in Table 6

| Lot # | % particles >20 microns | $D_{10}$ (μm) | $D_{50}$ (μm) | $D_{90}$ (μm) | $D_{90}/D_{10}$ |
|---|---|---|---|---|---|
| 00339-006 | 9.3 | 40.3 | 90.2 | 158.6 | 3.9 |
| 00339-009 | 9.8 | 33.6 | 54.2 | 115.9 | 3.4 |
| 00339-015 | 8.6 | 54.6 | 105.3 | 152.4 | 2.8 |
| 00300-140 | 9 | 83 | 117.6 | 151.9 | 1.8 |
| 00339-040 | 7.8 | 32.3 | 56.6 | 125.3 | 3.9 |
| 00339-027v | 9.8 | 49.5 | 85.2 | 130.2 | 2.6 |
| 00339-033 | 7.7 | 46.8 | 86.5 | 158 | 3.4 |
| 00300-143 | 9.2 | 83.17 | 117.9 | 152.9 | 1.8 |

Example 7

Varying Parameters in Process Using Workhead Assemblies

Certain process parameters were varied in processes using the modified workhead assemblies described in Example 1. Microparticles were prepared from a 75:25 poly(lactide-co-glycolide) (75% lactide, 25% glycolide) having an intrinsic viscosity of about 0.4 dL/g. (available from LAKESHORE BIOMATERIALS, 756 Tom Martin Drive Birmingham, Ala. 35211). The dispersed phase comprised 20 weight % of the polymer in ethyl acetate. The continuous phase comprised 1 weight % of polyvinyl alcohol in a solution saturated as 7.5% ethyl acetate. The batch size was 10 grams. The microparticles were collected on a 20 μm screen, and then freeze-dried. Yields are based on initial input of polymer and the weight of the microparticles collected after sieving on a 20 micron screen and freeze drying. A 125 μm scalping screen was not used. In the set of experiments, the continuous phase flow rate, CP/DP ratio, rotor speed, screen pore size, dispersed phase tube diameter, and dispersed phase tube position, relative to the screen, were all varied in different process runs. The process parameters are shown in Table 6 and 8, and the particle properties observed in particles prepared using these process parameters are shown in Tables 7 and 9, respectively. The screen used with process parameters shown in Table 6 was 125 μm. The screen used with process parameters shown in Table 8 was 75 μm. For process parameters shown in Table 8, the dispersed phase tube position was placed at a short distance from the screen.

Figure 5:
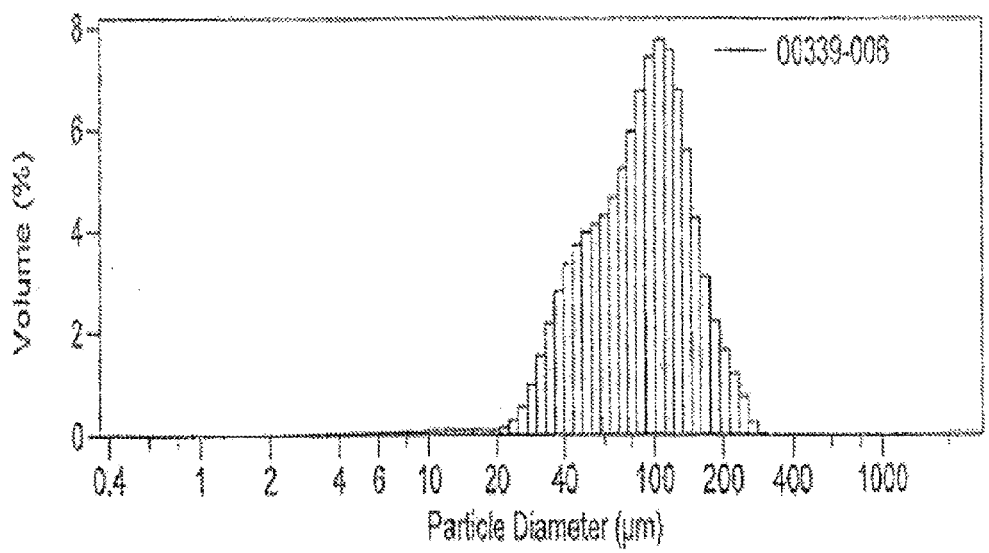
FIGS. 5-12 are plots of particle diameter distribution derived from data obtained from microparticle batches of Example 7 described below.
Figure 6:
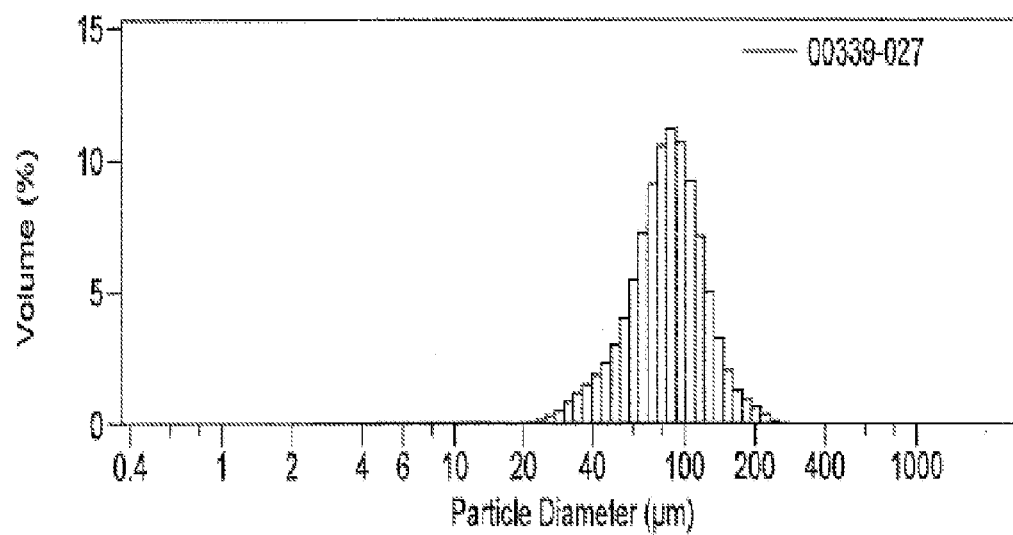
Figure 7:
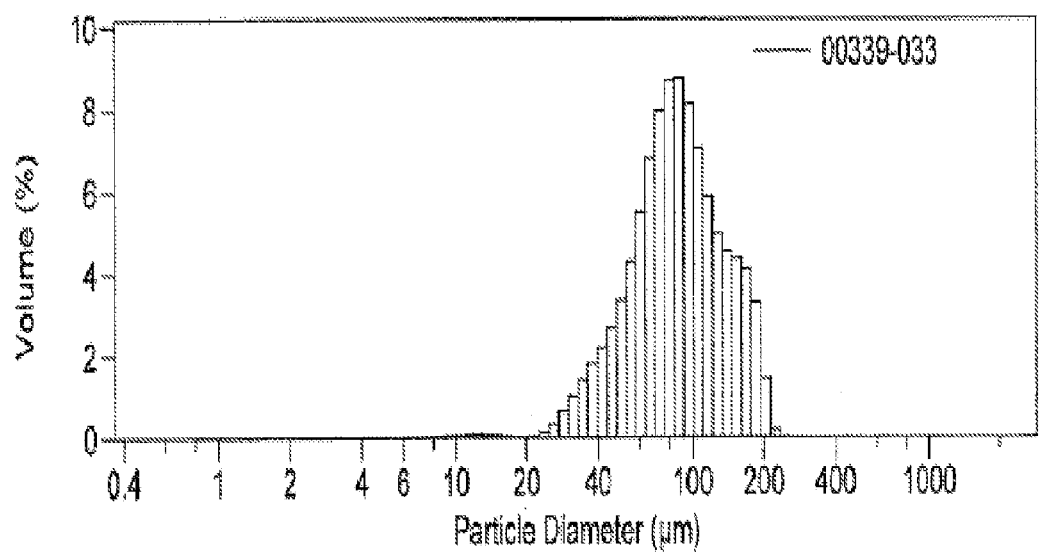
Figure 8:
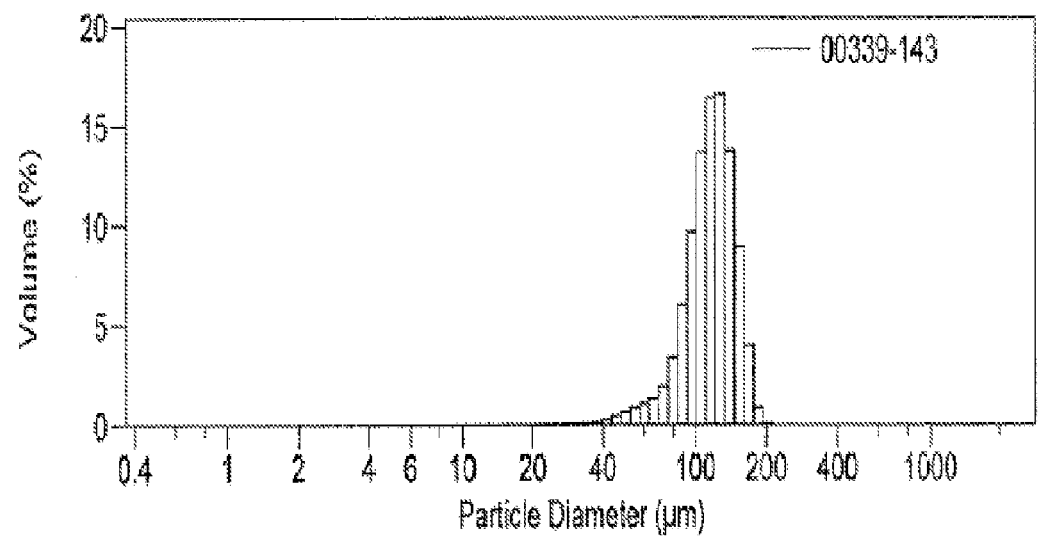

Plots of particle size distribution for Lot #s 00339-006 and 00339-027 are shown in FIGS. 5 and 6, respectively. These lots were prepared with the dispersed phase tube 0.25 inches away from the screen. Plots of particle size distribution for Lot #s 00339-033 and 00339-143 are shown in FIGS. 7 and 8, respectively. These lots were prepared with the dispersed phase tube roughly at the position of the screen, or about 0 cm away from the screen.

Results from Table 7 show that by using a screen size of 125 microns while changing CP flowrate, tube position, tube diameter, rotor speed and CP/DP ratio, a number of particle sizes could be generated. In general, faster speeds flowrates and smaller tube diameters generated smaller particle sizes. In 4 of the 8 formulations, particle sizes of less than 130 microns were generated with the 125 micron screen. All batches showed exceptionally high yields of greater than 80%.

TABLE 8

Process parameters

| Lot # | CP Flow rate (g/min) | CP/DP | Workhead speed (RPM) | DP Tube diameter (inches) |
|---|---|---|---|---|
| 00339-051 | 200 | 5 | 600 | 0.125 |
| 00339-098 | 200 | 10 | 800 | 0.25 |
| 00339-054 | 200 | 10 | 800 | 0.125 |
| 00339-116 | 125 | 10 | 800 | 0.25 |
| 00339-113 | 125 | 5 | 600 | 0.25 |
| 00339-057 | 125 | 5 | 800 | 0.125 |
| 00339-072 | 200 | 5 | 800 | 0.125 |
| 00339-110 | 200 | 10 | 600 | 0.25 |
| 00339-063 | 125 | 10 | 600 | 0.125 |
| 00339-101 | 200 | 5 | 800 | 0.25 |
| 00300-069 | 125 | 10 | 800 | 0.125 |
| 00339-104 | 200 | 5 | 600 | 0.25 |
| 00339-107 | 125 | 10 | 600 | 0.25 |
| 00339-066 | 125 | 5 | 600 | 0.125 |
| 00339-119 | 125 | 5 | 800 | 0.25 |
| 00339-095 | 200 | 10 | 600 | 0.125 |

TABLE 9

Results obtained from process using parameters listed in Table 8

| Lot # | % particles >20 microns | $D_{10}$ (μm) | $D_{50}$ (μm) | $D_{90}$ (μm) | $D_{90}/D_{10}$ |
|---|---|---|---|---|---|
| 00339-051 | 9.75 | 37.78 | 78.68 | 234.4 | 6.2 |
| 00339-098 | 9.7 | 36.48 | 89.78 | 434.3 | 11.9 |
| 00339-054 | 9.88 | 28.79 | 67.21 | 165.8 | 5.7 |
| 00339-116 | 8.3 | 25.71 | 38.94 | 68.87 | 2.7 |
| 00339-113 | 8.4 | 26.25 | 41.12 | 79.11 | 3.0 |
| 00339-057 | 8.2 | 26.22 | 39.18 | 71.39 | 2.7 |
| 00339-072 | 9.9 | 31.26 | 62.66 | 141 | 4.5 |
| 00339-110 | 9.5 | 40.75 | 123.5 | 205.8 | 5.0 |
| 00339-063 | 8.43 | 27.3 | 41.26 | 69.23 | 2.5 |
| 00339-101 | 9.7 | 38.73 | 98.19 | 251.3 | 6.5 |
| 00300-069 | 9.27 | 22.99 | 45.01 | 88.76 | 3.9 |
| 00339-104 | 8.67 | 26.13 | 54.68 | 195 | 7.5 |
| 00339-107 | 9.5 | 23.9 | 40.55 | 119 | 5.0 |
| 00339-066 | 8.8 | 26.35 | 41.62 | 83.76 | 3.1 |
| 00339-119 | 8.6 | 27.72 | 45.38 | 87.25 | 3.1 |
| 00339-095 | 9.63 | 36.89 | 63.11 | 171.9 | 4.6 |

Figure 9:
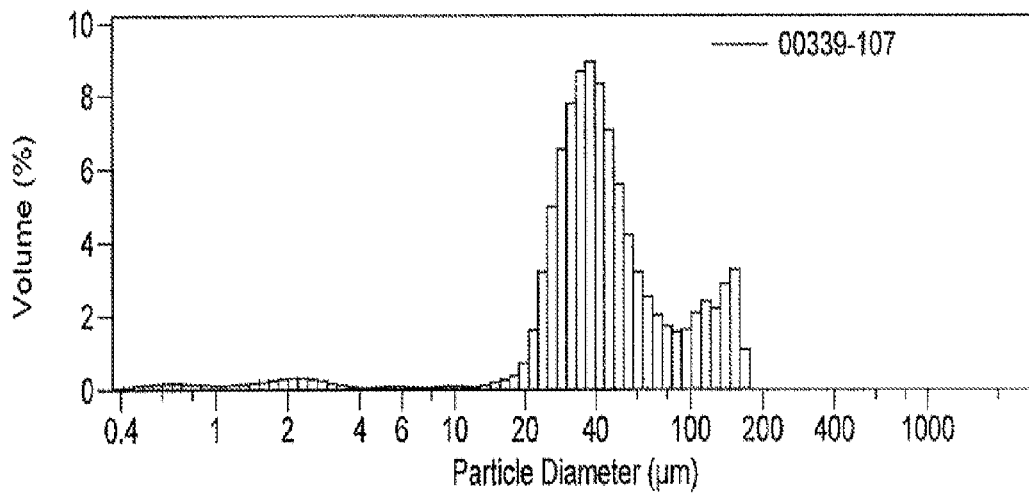
Figure 10:
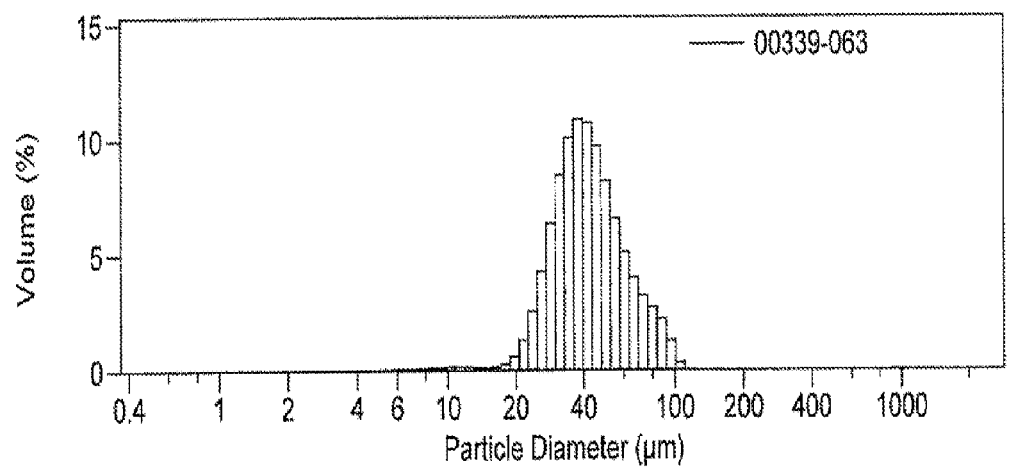
Figure 11:
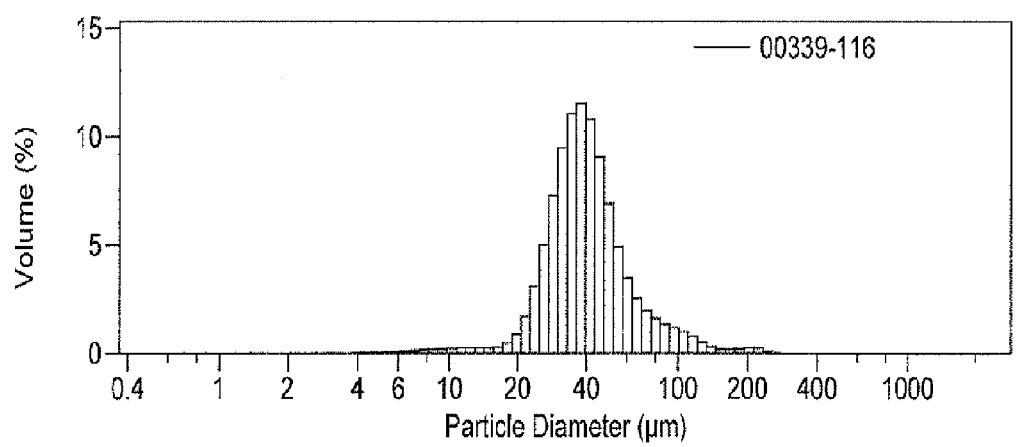
Figure 12:
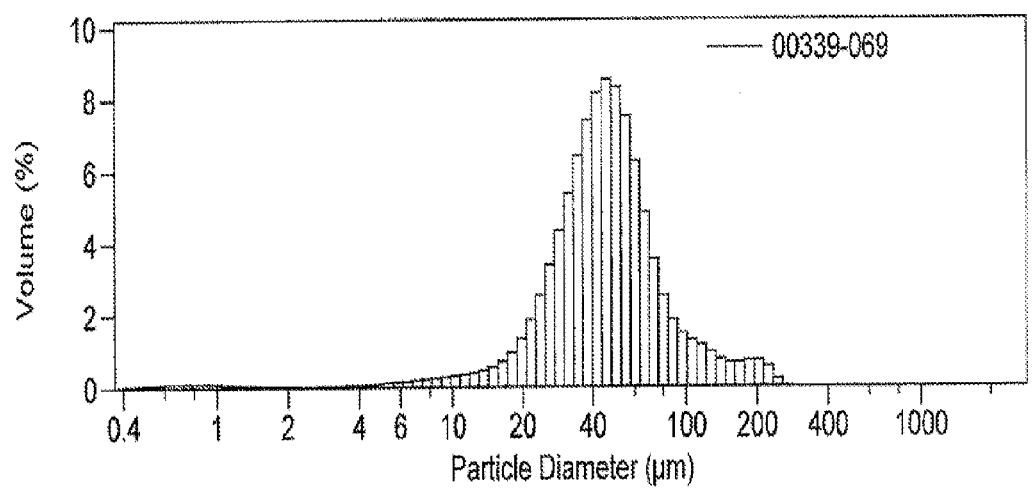

Plots of particle size distribution for Lot #s 00339-107 and 00339-063 are shown in FIGS. 9 and 10, respectively. These lots were prepared with the dispersed phase tube 0.25 inches away from the screen. Plots of particle size distribution for Lot #s 00339-116 and 00339-069 are shown in FIGS. 11 and 12, respectively. These lots were prepared with the dispersed phase tube roughly at the position of the screen, or about 0.125 inches away from the screen.

Results from Table 9 show that higher CP flowrates and larger DP tube diameter tended to generate larger particles sizes. Changing rotor speed, CP/DP ratio or CP flowrate tended to offset the influence of the tube diameter. In general, batches with low $D_{90}/D_{10}$ size ratio had $D_{90}$ sizes of around 70 microns. The influence of the 75 micron screen generating particles less than its pore size is shown here. The use of the 75 micron screen helped generate desirable particles sizes that could be used in an injectable microparticle product.

As shown in both Table 7 and Table 9, microparticle product yields were in excess of 75%. In some instances, yields of greater than 90% were obtained while having acceptable particle size. In no case in the collection was a 125 micron screening step used to remove larger size particles. Particle size analysis showed in some cases an absence of particles greater than 125 microns while an exceptionally high yield was obtained, e.g. Lot #00339-063.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. A process for making microparticles, comprising:
   (a) providing a process stream comprising (i) a dispersed phase comprising a first solvent having a polymer and an agent dissolved or dispersed therein; and (ii) a continuous phase comprising a second solvent that is partially or totally immiscible in the first solvent;
   (b) passing the process stream through a screen and into a mixing environment, without a subsequent screen or perforated stator in the mixing environment; such that during step (a) and/or (b), an emulsion forms that comprises microdroplets of the dispersed phase in the continuous phase;
   (c) at least substantially removing the first solvent from the microdroplets to form the microparticles; and wherein the process is performed without high-shear mixing, wherein the process stream is not subsequently screened in the mixing environment.

2. The process of claim 1, wherein the first solvent is an organic solvent.

3. The process of claim 1, wherein the second solvent is an aqueous solvent.

4. The process of claim 1, wherein the continuous phase further comprises a surfactant.

5. The process of claim 1, wherein the polymer is a biodegradable or biocompatible polymer.

6. The process of claim 1, wherein the polymer comprises poly(lactide), poly(glycolide), poly(caprolactone), or a copolymer or mixture thereof.

7. The process of claim 1, wherein the agent is a bioactive agent.

8. The process of claim 1, wherein the solvent removal step is performed by freeze-drying or cryogenic extraction.

9. A process for making microparticles, comprising:
   (a) providing a process stream comprising: a primary emulsion comprising microdroplets of (i) a first dispersed phase comprising a first solvent having an agent dissolved or dispersed therein, and (ii) a second dispersed phase comprising a second solvent that is partially or totally immiscible in the first solvent and having a polymer dissolved or dispersed therein; and a continuous phase comprising a third solvent that is partially or totally immiscible in the second solvent;
   (b) passing the process stream through a screen and into a mixing environment; such that during steps (a) or (b), a double-emulsion forms comprising the first and second dispersed phases in the continuous phase; and
   (c) at least substantially removing the second solvent from the double-emulsion to form the microparticles; and wherein the process is performed without high-shear mixing, wherein the process stream is not subsequently screened in the mixing environment.

10. The process of claim 9, wherein the first solvent is an aqueous solvent.

11. The process of claim 9, wherein the second solvent is an organic solvent.

12. The process of claim 9, wherein the third solvent is an aqueous solvent.

13. The process of claim 9, wherein the continuous phase further comprises a surfactant.

14. The process of claim 9, wherein the polymer is a biodegradable polymer.

15. The process of claim 9, wherein the polymer comprises poly(lactide), poly(glycolide), poly(caprolactone), or a copolymer or mixture thereof.

16. The process of claim 9, wherein the agent is a bioactive agent.

* * * * *